United States Patent
Ortac (10) Patent No.: US 11,486,000 B2
(45) Date of Patent: *Nov. 1, 2022

(54) METHODS FOR SINGLE MOLECULE SEQUENCING

(71) Applicant: SARMAL, INC., San Diego, CA (US)

(72) Inventor: Inanc Ortac, San Diego, CA (US)

(73) Assignee: SARMAL, INC., San Diego, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 16/470,116

(22) PCT Filed: Dec. 15, 2017

(86) PCT No.: PCT/US2017/066823
§ 371 (c)(1),
(2) Date: Jun. 14, 2019

(87) PCT Pub. No.: WO2018/112412
PCT Pub. Date: Jun. 21, 2018

(65) Prior Publication Data
US 2019/0360038 A1    Nov. 28, 2019

Related U.S. Application Data

(60) Provisional application No. 62/435,166, filed on Dec. 16, 2016.

(51) Int. Cl.
*C12Q 1/68* (2018.01)
*C12Q 1/6869* (2018.01)

(52) U.S. Cl.
CPC ................... *C12Q 1/6869* (2013.01)

(58) Field of Classification Search
CPC ..................................... C12Q 1/6869
See application file for complete search history.

(56) References Cited

U.S. PATENT DOCUMENTS

2012/0034602 A1    2/2012   Emig et al.
2012/0329042 A1    12/2012  Beechem et al.

OTHER PUBLICATIONS

Seidel et al. J. Phys. Chem. 1996, 100, 5541-5553 (Year: 1996).*
International Search Report of PCT Application No. PCT/US2017/066823, dated Mar. 9, 2018, 3 pages.
Written Opinion of PCT Application No. PCT/US2017/066823, dated Mar. 9, 2018, 5 pages.

* cited by examiner

*Primary Examiner* — Jezia Riley
(74) *Attorney, Agent, or Firm* — Procopio, Cory, Hargreaves & Savitch LLP (57) ABSTRACT

Provided herein are methods and systems for sequencing a single nucleic acid molecule utilizing a polymerase enzyme, a template nucleic acid, and a polymerase reagent solution.

13 Claims, 5 Drawing Sheets

METHODS FOR SINGLE MOLECULE SEQUENCING

CROSS REFERENCE TO RELATED APPLICATIONS

This application is a U.S. National Stage entry of PCT Application No. PCT/US2017/066823, filed Dec. 15, 2017, which claims priority to U.S. Provisional Patent Application No. 62/435,166, filed Dec. 16, 2016, the contents of each of which are incorporated herein by reference in their entirety.

TECHNICAL FIELD

The invention relates to methods for single molecule nucleic acid sequencing.

INTRODUCTION

Current sequencing technologies can be grouped into two main categories: short-read sequencing and long-read sequencing. In each category, DNA is cleaved into pieces with lengths up to a certain number of nucleotides or basepairs (bp). In all cases, all pieces of DNA are spread into a 2 dimensional array and are detected by a sensor array corresponding to where at least one sensor is matched with a piece of DNA.

Short-read sequencing approaches are simple cycle based technologies that includes sequencing-by-ligation (SBL) and sequencing-by-synthesis (SBS). SBL approaches includes SOLID (Thermo Fisher) and Complete Genomics (BGI). With SOLID, read lengths around 75 basepairs (bps) is reached while with Complete Genomics approach 28 to 100 basepair reads are feasible. With these approaches structural variation and genome assembly is not possible and they are susceptible to homopolymer errors. Their runtimes are on the order of several days. Illumina and Qiagen's GeneReader technology use SBS approach with Cyclic Reversible Termination. They can reach up to 300 bp. However, a major drawback is under representation of AT and GC rich regions, substation errors and high half positive rate. On the other hand, other SBS approaches such as 454 pyrosequencing and Ion Torrent (Thermo Fisher) use single-nucleotide Addition/Termination. 454 pyrosequencing could reach 400 bp while Ion Torrent can achieve 700 bp read lengths. However, although these technologies are faster and good for point of care, they also have many drawbacks including domination of insertion/deletion errors, and homopolymer region errors. They cannot be used to reveal long-range genomic or transcriptomic structure, and cannot do paired end sequencing.

Long-read sequencing approaches include two main types, synthetic long-read sequencing or real-time long-read sequencing. Synthetic long-read sequencing used by Illumina and 10× Genomics focuses on library preparation that leverages barcodes and allows computational assembly of large fragments. In fact, these technologies do not do actual long-reads, rather they do short-reads, in which the DNA pieces are organized using a barcoding approach, which helps eliminate some complexity during analysis, which allows obtaining data similar to actual long-read methods. However, this approach has a very high cost due, in part, to its requiring even more coverage. The other type of long-read sequencing is real-time long-read sequencing, which has been used by Pacific Biosciences and Oxford Nanopore Technologies. Unlike synthetic long-read sequencing, real-time long-read sequencing does not rely on clonal population of amplified DNA and does not require chemical cycling. Nanopore's technology has very high error rates around 30%, which also require very high coverage that contributes significantly to the cost. Using modified bases has also been particularly challenging for Nanopore's technology, which has generated unique signals that makes the analysis even more complex. Pacific Biosciences can reach read lengths up to 4000-5000 bps. However, due to high single-pass error rates around 15% for long reads, high coverage is required, which makes 1 Gb sequencing cost more than $1000 (see., e.g., Goodwin et al., Nat. Rev. Genet. 17:333-351; 2016).

Since, a large majority of current technologies offer short read lengths (around 40-100 bases long) of nucleotides per unit, one of the most challenging problem lies in alignment of small pieces of sequences into one large meaningful sequence, and analyzing high coverage data and the post-processing of the loads of generated data with complicated algorithms using powerful super computers. Newer generation single molecule based sequencing technologies can potentially address this issue. However, each of these prior art technologies have high error rates requiring high coverages (multiple reads of the same region of a sequence) often around 30× to 100× in order to obtain a reliable data.

Accordingly, there is a need for improved methods for single molecule nucleic acid sequencing.

SUMMARY

Provided herein are methods for sequencing a nucleic acid template comprising:

providing a sequencing mixture comprising (i) a polymerase enzyme, (ii) a template nucleic acid, and (iii) a polymerase reagent solution having the components for carrying out template directed synthesis of a growing nucleic acid strand, wherein said polymerase reagent solution includes a component for a requenching reaction (e.g., a quenching enzyme, and the like) and a plurality of types of nucleotide analogs; wherein each type of nucleotide analog has a labeled leaving group that is cleavable by the polymerase, and each type of nucleotide analog has a different label, wherein the labeled leaving group is cleaved upon polymerase-dependent binding of a respective nucleotide analog to the template strand;

carrying out nucleic acid synthesis such that a plurality of nucleotide analogs are added sequentially to the template whereby: a) a nucleotide analog associates with the polymerase, b) the nucleotide analog is incorporated on the template strand by the polymerase when the labeled leaving group on that nucleotide analog is cleaved by the polymerase, wherein the labeled leaving group emits light upon cleavage, then c) the labeled leaving group on the nucleotide analog is quenched by the requenching reaction; and detecting light from the labels while nucleic acid synthesis is occurring, and using light detected in the time between step b) when the labelled leaving group is cleaved, and step c) in which the labeled leaving group is quenched, to determine a sequence of the template nucleic acid.

The invention methods are useful for a variety of uses including whole genome sequencing and SNP-variant detection.

Figure 1:
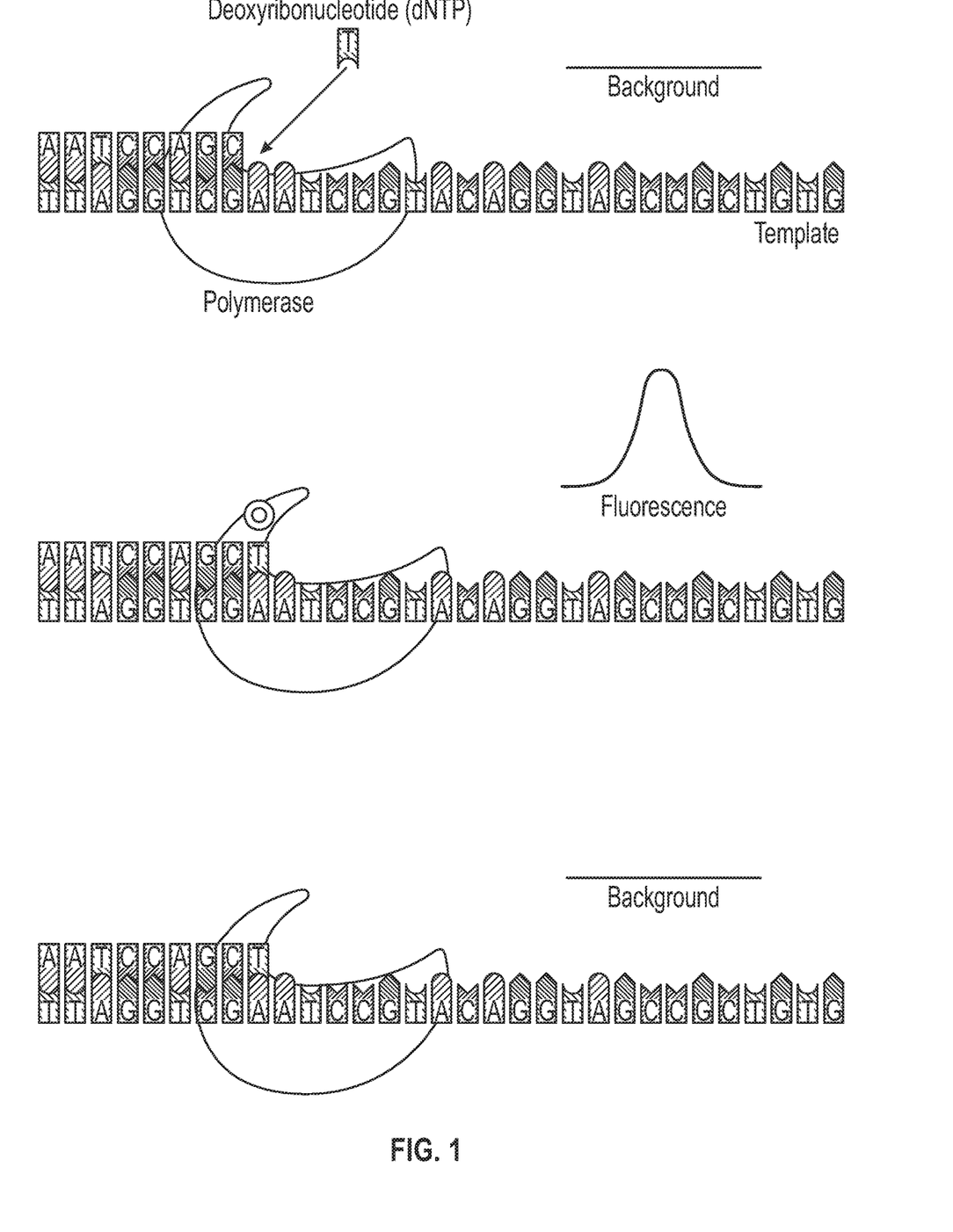
FIG. 1 shows a general illustration of one embodiment of the invention sequencing method: DNA Polymerase uses modified dNTPs with initially quenched fluorophores as building blocks. Upon binding to polymerase, the fluorescent molecule become activated and later it is cleaved off, detected, and finally is quenched.

The disclosed invention is a single molecule sequencing technology based on monitoring individual polymerase enzymes as they incorporate dNTPs sequentially. In a particular embodiment, the invention encompasses a process where each time polymerase incorporates a dNTPs complementary to the template, a fluorescence signal is generated during the incorporation process and subsequently is quenched once the incorporation process ends. The process repeats for the next dNTP incorporation (FIG. 1).

More particularly, each time a polymerase incorporates a modified deoxyribonuleoside triphosphate (dNTP) nucleotide analog to the strand complementary to the template DNA, a fluorescence signal specific to the type of the nucleotide attached is generated. There are four types of dNTPs, namely deoxyadenosine triphosphate (dATP), deoxyguanosine triphosphate (dGTP), deoxycytidine triphosphate (dCTP), and deoxythymidine triphosphate (dTTP). Each nucleotide generates a unique fluorescence signal (e.g., in red, yellow, green, or blue, and the like) while they are being attached to the complementary strand by the polymerase enzyme. Upon the completion of attachment of the nucleotide analog to the 3' moiety of the previously attached nucleotide analog, the fluorescence generated by the leaving group is detected by an appropriate fluorescence sensor and/or detection device and then it is subsequently rapidly quenched (FIG. 1).

Sequencing is achieved by detecting the fluorescence generated each time a nucleotide is added to the complementary strand revealing the type of nucleotide. Therefore, each specific nucleotide attachment generates a short peak of a fluorescence signal that can be detected by a fluorescence sensor. As a result a data array of succeeding, sequential colors is produced, which can be converted into a corresponding data array of nucleotide sequence (FIG. 1).

An advantage provided by the invention methods disclosed herein lies in its simplicity and innovative chemistry that significantly reduces background signal during detection thereby improving sensitivity. In accordance with the present invention methods, less modification of the reaction conditions involving reagents and enzymes improves specificity, efficiency and rate. Also in accordance with the present invention methods, polymerase operates in near ideal conditions, and is contemplated to reach very long read lengths around tens of thousands of bases per DNA polymerase molecule by utilizing high sensitivity and specificity together with requiring significantly less post-processing and analysis of the data produced. The combined features of the invention methods disclosed herein reduces the cost both for the respective devices and each run, while achieving high specificity in addition to decreasing the time per test considerably compared to competing technologies. Accordingly, the disclosed invention methods and systems allow realization of very low cost and real-time sequencing systems without adversely affecting specificity.

INCORPORATION BY REFERENCE

Herein, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

DETAILED DESCRIPTION

Provided herein are methods for sequencing a nucleic acid template comprising:

providing a sequencing mixture comprising (i) a polymerase enzyme, (ii) a template nucleic acid, and (iii) a polymerase reagent solution having the components for carrying out template directed synthesis of a growing nucleic acid strand, wherein said polymerase reagent solution includes a component for a requenching reaction (e.g., a quenching enzyme, and the like) and a plurality of types of nucleotide analogs; wherein each type of nucleotide analog has a labeled leaving group that is cleavable by the polymerase, and each type of nucleotide analog has a different label, wherein the labeled leaving group is cleaved upon polymerase-dependent binding of a respective nucleotide analog to the template strand;

carrying out nucleic acid synthesis such that a plurality of nucleotide analogs are added sequentially to the template whereby: a) a nucleotide analog associates with the polymerase, b) the nucleotide analog is incorporated on the template strand by the polymerase when the labeled leaving group on that nucleotide analog is cleaved by the polymerase, wherein the labeled leaving group emits light upon cleavage, then c) the labeled leaving group on the nucleotide analog is quenched by the requenching reaction; and detecting light from the labels while nucleic acid synthesis is occurring, and using light detected in the time between step b) when the labelled leaving group is cleaved, and step c) in which the labeled leaving group is quenched, to determine a sequence of the template nucleic acid.

As used herein a "polymerase enzyme" refers to the well known protein responsible for carrying out nucleic acid synthesis. A preferred polymerase enzyme for use herein is a DNA polymerase. In natural polymerase mediated nucleic acid synthesis, a complex is formed between a polymerase enzyme, a template nucleic acid sequence, and a priming sequence that serves as the point of initiation of the synthetic process. During synthesis, the polymerase samples nucleotide monomers from the reaction mix to determine their complementarity to the next base in the template sequence. When the sampled base is complementary to the next base, it is incorporated into the growing nascent strand. This process continues along the length of the template sequence to effectively duplicate that template. Although described in a simplified schematic fashion, the actual biochemical process of incorporation can be relatively complex. A diagrammatical representation of the incorporation biochemistry is provided in FIG. 4. This diagram is not a complete description of the mechanism of nucleotide incorporation. During the reaction process, the polymerase enzyme undergoes a series of conformational changes which can be essential steps in the mechanism.

Figure 4:
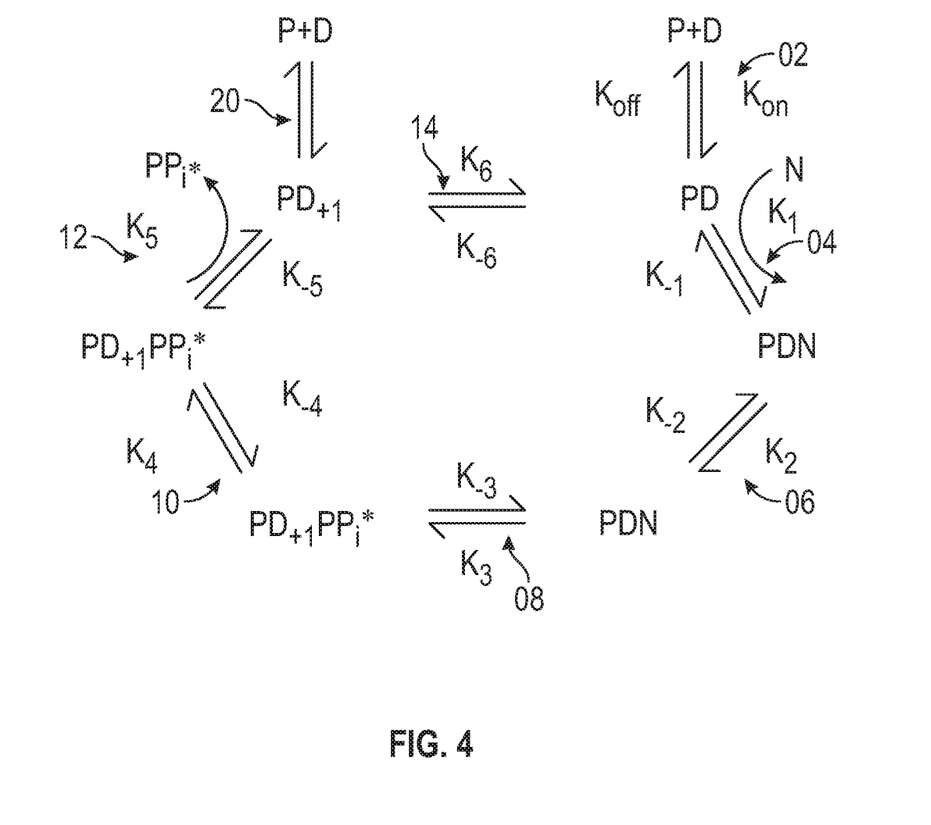
FIG. 4 shows a simplified schematic of the biochemical process of dNTP incorporation into a template strand.

As shown in FIG. 4, the synthesis process begins with the binding of the primed nucleic acid template (D) to the polymerase (P) at step 2. Nucleotide (N) binding with the complex occurs at step 4. Step 6 represents the isomerization of the polymerase from the open to closed conformation. Step 8 is the chemistry step in which the nucleotide is incorporated into the growing strand. At step 10, polymerase isomerization occurs from the closed to the open position. The polyphosphate component that is cleaved upon incorporation is released from the complex at step 12. While the figure shows the release of pyrophosphate, it is understood that when a labeled nucleotide or nucleotide analog is used, the component released may be different than pyrophosphate. In many cases, the systems and methods of the invention use a nucleotide analog having a label on its terminal phosphate, such that the released component comprises a polyphosphate connected to a dye (e.g., a label pyrophosphate; $PP_i$). With a natural nucleotide or nucleotide analog substrate, the polymerase then translocates on the template at step 14. After translocation, the polymerase is in the position to add another nucleotide and continue around the reaction cycle.

Preferred polymerase enzymes for use herein include DNA polymerases, which can be classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderrna pigmentosum variant (class Y). For a review of nomenclature, see, e.g., Burgers et al. (2001) "Eukaryotic DNA polymerases: proposal for a revised nomenclature" J Biol Chem. 276(47):43487-90. For a review of polymerases, see, e.g., Hubscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398; each of which are incorporated herein by reference in their entirety. The basic mechanisms of action for many polymerases have been determined. The sequences of literally hundreds of polymerases are publicly available, and the crystal structures for many of these have been determined, or can be inferred based upon similarity to solved crystal structures for homologous polymerases.

Many such polymerases suitable for nucleic acid sequencing are readily available. For example, human DNA Polymerase Beta is available from R&D systems. Preferred DNA polymerase for use herein, include DNA polymerase I that is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. PHI.29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Other commercial DNA polymerases include PhusionhM High-Fidelity DNA Polymerase, available from New England Biolabs; GoTaq®. Flexi DNA Polymerase, available from Promega; RepliPHI-™.PHI.29 DNA Polymerase, available from Epicentre Biotechnologies; PfuUltra™ Hotstart DNA Polymerase, available from Stratagene; KOD HiFi DNA Polymerase, available from Novagen; and many others.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584, 481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, PHI-29 related polymerases including wild type PHI-29 polymerase and derivatives of such polymerases such as exonuclease deficient forms, T7 DNA polymerase, T5 DNA polymerase, an RB69 polymerase, etc.

In addition, the polymerases can be further modified for application-specific reasons, such as to increase photostability, e.g., as taught in U.S. patent application Ser. No. 12/384,110 filed Mar. 30, 2009, to improve activity of the enzyme when bound to a surface, as taught, e.g., in WO 2007/075987, and WO 2007/076057, or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

As used herein, the phrase "template nucleic acid" refers to any suitable polynucleotide, including double-stranded DNA, single-stranded DNA, single-stranded DNA hairpins, DNA/RNA hybrids, RNAs with a recognition site for binding of the polymerizing agent, and RNA hairpins. Further, target polynucleotides suitable as template nucleic acids for use in the invention sequencing methods may be a specific portion of a genome of a cell, such as an intron, regulatory region, allele, variant or mutation; the whole genome; or any portion thereof. In other embodiments, the target polynucleotides may be mRNA, tRNA, rRNA, ribozymes, antisense RNA or RNAi. The target polynucleotide may be of any length, such as at between about 10 bases up to about 100,000 bases, between about 10,000 bases up to about 90,000 bases, between about 20,000 bases up to about 80,000 bases, between about 30,000 bases up to about 70,000 bases, between about 40,000 bases up to about 60,000 bases, or longer, with a typical range being between about 10,000-50,000 bases. Also contemplated herein are target template nucleic acid lengths of between about 100 bases and 10,000 bases.

The template nucleic acids of the invention can also include unnatural nucleic acids such as PNAs, modified oligonucleotides (e.g., oligonucleotides comprising nucleotides that are not typical to biological RNA or DNA, such as 2'-O-methylated oligonucleotides), modified phosphate backbones and the like. A nucleic acid can be e.g., single-stranded or double-stranded.

As used herein, the phrase "nucleotide analog" refers to modified nucleotides that can be used in DNA synthesis (e.g., modified dNTPs such dATP, dTTP, dGTP, dCTP and dUTP). The nucleotide analogs for use in the invention can be any suitable nucleotide analog that is capable of being a substrate for the polymerase and for the selective cleaving activity. It has been shown that nucleotides can be modified and still used as substrates for polymerases and other enzymes. Where a variant of a nucleotide analog is contemplated, the compatibility of the nucleotide analog with the polymerase or with another enzyme activity such as exonuclease activity can be determined by activity assays. The carrying out of activity assays is straightforward and well known in the art.

The nucleotide analog can be, for example, a nucleoside polyphosphate having three or more phosphates in its polyphosphate chain with a label on the portion of the polyphosphate chain that is cleaved upon incorporation into the growing strand. The polyphosphate can be a pure polyphosphate, e.g. —O—PO3- or a pyrophosphate (e.g., $PP_i$), or the polyphosphate can include substitutions. Additional details regarding analogs and methods of making such analogs can be found in U.S. Pat. Nos. 7,405,281; 9,464,107, and the like; incorporated herein by reference in its entirety for all purposes.

Alternative labeling strategies may employ inorganic materials as labeling moieties, such as fluorescent or luminescent nanoparticles, e.g. nanocrystals, i.e. Quantum Dots, that possess inherent fluorescent capabilities due to their semiconductor make up and size in the nanoscale regime (See, e.g., U.S. Pat. Nos. 6,861,155, 6,699,723, 7,235,361, which are incorporated by reference herein for all purposes). Such nanocrystal materials are generally commercially available from, e.g., Life Technologies, (Carlsbad Calif.). Again, such compounds may be present as individual labeling groups or as interactive groups or pairs, e.g., with other inorganic nanocrystals or organic fluorophores. In some cases fluorescent proteins can be used such as green fluorescent protein (GFP, EGFP), blue fluorescent protein (EBFP, EBFP2, Azurite, mKalamal) cyan fluorescent protein (ECFP, Cerulean, CyPet) and yellow fluorescent protein derivatives (YFP, Citrine, Venus, YPet). Also contemplated for use herein is fluorescent cell barcoding using multipole fluorescence dyes procuding multiple color coded signals for detection, such as described in Krutzek et al., Curr Protoc Cytom. 2011 January; CHAPTER: Unit-6.31. (doi:10.1002/0471142956.cy0631s55.); which is incorporated herein by reference in its entirety for all purposes.

In a preferred embodiment, the nucleotide analog is modified by adding a fluorophore to a terminal phosphate (see, e.g, Yarbrough et al., J. Biol. Chem., 254:12069-12073, 1979; incorporated herein by reference in its entirety for all purposes), such that when the $PP_i$ labeled leaving group is generated by the polymerase when the nucleotide analog is incorporated into the template strand. In this embodiment, the fluorophore is attached in such a way so that the fluorescent signal is quenched by the respective nucleobase as set forth, for example, in Seidal et al, J Phys. Chem., 1996, 100:5541-5553, incorporated herein by reference in its entirety for all purposes. There are four types of dNTPs, namely deoxyadenosine triphosphate (dATP), deoxyguanosine triphosphate (dGTP), deoxycytidine triphosphate (dCTP), and deoxythymidine triphosphate (dTTP). In preferred embodiments of the invention methods disclosed herein, each respective dNTP is modified using a different, unique fluorophore relative to the other dNTPs, such that each time a polymerase incorporates a modified deoxyribonuleoside triphosphate (dNTP) nucleotide analog to the strand complementary to the template DNA, a fluorescence signal specific to the class or type of the nucleotide (e.g., unique signals for each of dATP, dTTP, dGTP and dCTP) attached is generated.

In another embodiment, to the nucleotide analog that already has a quenched fluorophore therein, stronger quenching in the invention sequencing methods is achieved by binding an additional removable quencher molecule to that nucleotide analog, wherein the removable quencher molecule is also released (e.g., kicked-out) upon binding with polymerase. The utilization of this additional second quencher, in addition to the quenching by the nucleobase within the nucleotide analog, is referred to herein as dual-quenching of the respective nucleotide analog. In this particular embodiment of dual-quenching, a removable quencher can be attached or bound to the nucleotide analog before interacting with the polymerase through, for example, weak hydrogen bonding or electrostatic interaction (or the like) with the base or sugar of the nucleotide analog already having a fluorophore therein that is quenched by the respective nucleobase as set for above (FIG. 3). The resulting dual-quenching of the nucleotide analog fluorescent signal further enhances the fidelity of the invention sequencing method. In this embodiment, the quencher on APS (FIG. 2C) may be covalently attached as well as non-covalently attached. It is contemplated herein that APS used herein can have extra (e.g., more than 1) quenchers without adversely affecting the sequencing reaction.

Each nucleotide generates a unique fluorescence signal (e.g., in red, yellow, green, or blue, and the like) while they are being attached to the complementary strand by the polymerase enzyme. Upon the completion of attachment of the nucleotide analog to the 3' moiety of the previously attached nucleotide analog, the fluorescence generated by the leaving group (e.g., fluorescent pyrophosphate; PPi) is detected by an appropriate fluorescence sensor and/or detection device and then the labeled pyrophosphate is subsequently rapidly quenched (FIG. 1).

Using the invention methods provided herein, a particular signal indicating the particular type of nucleotide will be generated only during the specific interaction of the nucleotide with the polymerase. The pre- and post-polymerase interaction states will be similar; and the signal will "change" during the interaction with the polymerase. For example, in the fluorescence quenching embodiment described herein:
1—Initially, there is either no or very low background fluorescence.
2—During polymerase interaction, a specific type of fluorescence is generated.
3—After $PP_i$ release and the quenching reaction of pyrophosphate, the signal goes back to initial state.

In another embodiment employing Plasmonics, the proximity of metal nanoparticles changes the signal: plasmonic shift. For example, the base or sugar of a nucleotide has a metal nanoparticle attached, and the terminal phosphate has another metal nanoparticle attached. In another embodiment, this is also used to identify the respective type of base: via either different respective metals such as gold, silver, copper, aluminum, and the like; or metal particles having different diameters can be used:
1—Initially, each nucleotide has two metal nanoparticles that are coupled (plasmonically), which corresponds to a particular background plasmonic signal.
2—During polymerase interaction, with the release of the metal nanoparticle with the pyrophosphate, a plasmonic couple is broken creating a plasmonic shift following the release, which corresponds to the signal being detected for the respective nucleotide.
3—Afterwards, the released pyrophosphate with metal nanoparticle is attached to APS such that all the metal nanoparticles return to their initial coupled state.

In yet another embodiment, Fluorescence Resonance Energy Transfer (FRET) is contemplated for use herein instead of quenching another base signal. For example when utilizing FRET in the invention methods rather than a quenching reaction, there is an acceptor dye (a long wavelength such as red) on the base or sugar. In this embodiment, the fluorophores on the terminal phosphate are donors having shorter wavelengths (e.g., blue, green, yellow, orange), such that when combined they do FRET to the acceptor and we only see red fluorescence, which is the base signal. Then, after attachment and upon cleavage see their specific fluorescence until they are recombined with the secondary reaction to FRET and emit red again. Numerous donor:acceptor FRET pairs are well-known in the art for use herein. Briefly:

1—Initially, there is a particular fluorescence emission (e.g., "red").
2—During interaction with polymerase, a specific type of fluorescence is generated different than red (e.g., blue, green, yellow, orange).
3—After, release of pyrophosphate signal goes back to initial state ("red").

As used herein, the phrase "labeled leaving group" refers to the polyphosphate chain having a label, e.g., a fluorophore, or the like, attached therein, that is released from a respective dNTP when and/or upon cleavage by the polymerase enzyme (e.g., DNA pol) during the incorporation of the respective dNTP into the template nucleic acid strand. In a particular embodiment herein, the polyphosphate is a fluorescently labeled pyrophosphate (PPi) that is cleaved and released into the reaction mixture for subsequent fluorescence detection prior to the labeled pyrophosphate becoming quenched by a component for a requenching reaction (e.g., a quenching enzyme, and the like) as set forth herein (see FIG. 2B).

As used herein, the phrase "polymerase reagent solution" refers to the mixture of components necessary for carrying out the template directed synthesis of a growing nucleic acid. The polymerase reagent solution for use with a polymerase, e.g., DNA pol I, and the like, includes a quenching enzyme (e.g., ATP sulfurylase, and the like) and suitable concentrations of dNTPs, e.g., fluorophore-modified nucleotide analogs described herein. In a preferred embodiment, the concentrations of dNTPs employed are much higher than has been heretofore possible because, in part, of the low fluorescent background resulting from the labeled leaving groups (e.g., fluorescent pyrophosphate; $PP_i$) advantageously employed in the invention methods. Because the quenching enzyme (e.g., ATP sulfurylase) and polymerase rates can vary significantly depending on the type and source of the enzymes, the rate of quenching achieved by the ATP sulfurylase reaction employed herein can be adjusted separately by adjusting reaction conditions such as ATP sulfurylase concentration, and the like as described herein.

As used herein, the phrase "sequencing mixture" refers to the components that are used to carry out the invention single molecule sequencing reactions. In one embodiment, the sequencing mixture includes a polymerase enzyme (e.g., DNA pol I), a template nucleic acid, and a polymerase reagent solution including a component for a requenching reaction (e.g., a quenching enzyme, such as ATP sulfurylase, and the like) and labeled nucleotide analogs therein. In accordance with the present invention, the sequencing mixture used provides the following advantages in the invention sequencing methods over previous sequencing methods: the polymerase employed functions in its ideal state; there is no need to modify a polymerase enzyme; the use of high nucleotide (e.g., dNTP) concentrations results in optimum efficiency; requires only low intensity excitation light, which advantageously reduces photobleaching of the fluorophores and reduces the denaturing of the polymerase enzyme; provides virtually no fluorescent background, which improves specificity and sensitivity of the base calling; does not require sophisticated optics or nanostructured chip design, which reduces cost; it provides high specificity, which reduces the need for high coverage; and provides long read lengths (e.g., about 50 Kb to 1 gene/cell) with much less computer processing required relative to prior art methods.

Figure 2A:
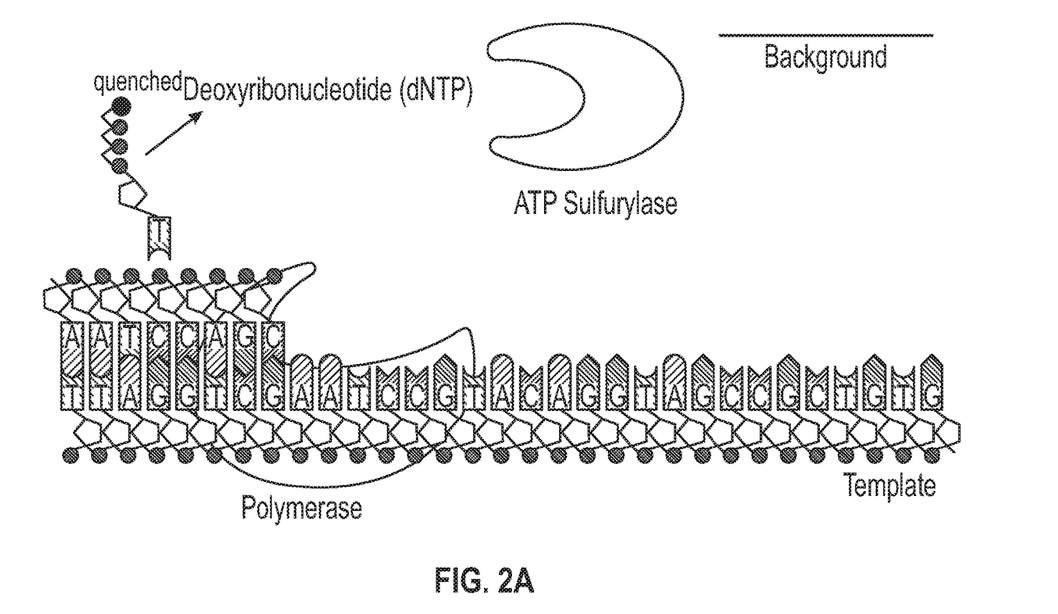
FIG. 2A shows a depiction of a fluorophore attached to the terminal phosphate of a dNTP, which is quenched by the respective nucleobase while the fluorophore is attached. Each respective nucleobase has a different quenching capability of the different fluorophores.
Figure 2B:
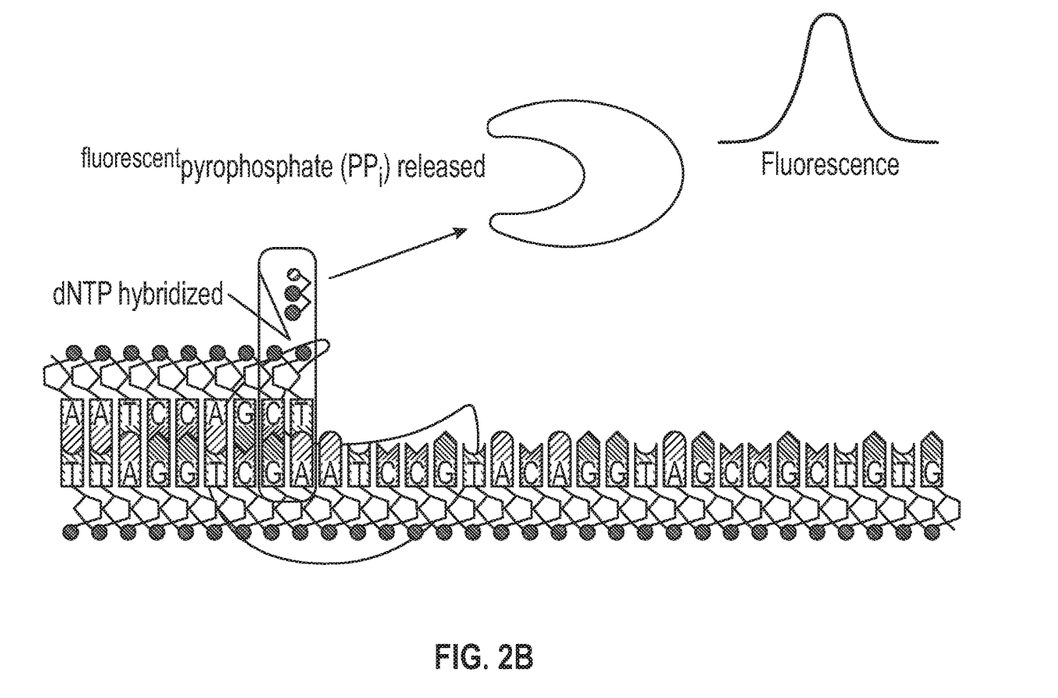
FIG. 2B shows the polymerase-dependent binding of a respective nucleotide analog having a fluorophore attached therein to the template strand and the cleaving of the labeled pyrophosphate that has the fluorophore attached, which causes the fluorophore to emit a fluorescence light signal.
Figure 2C:
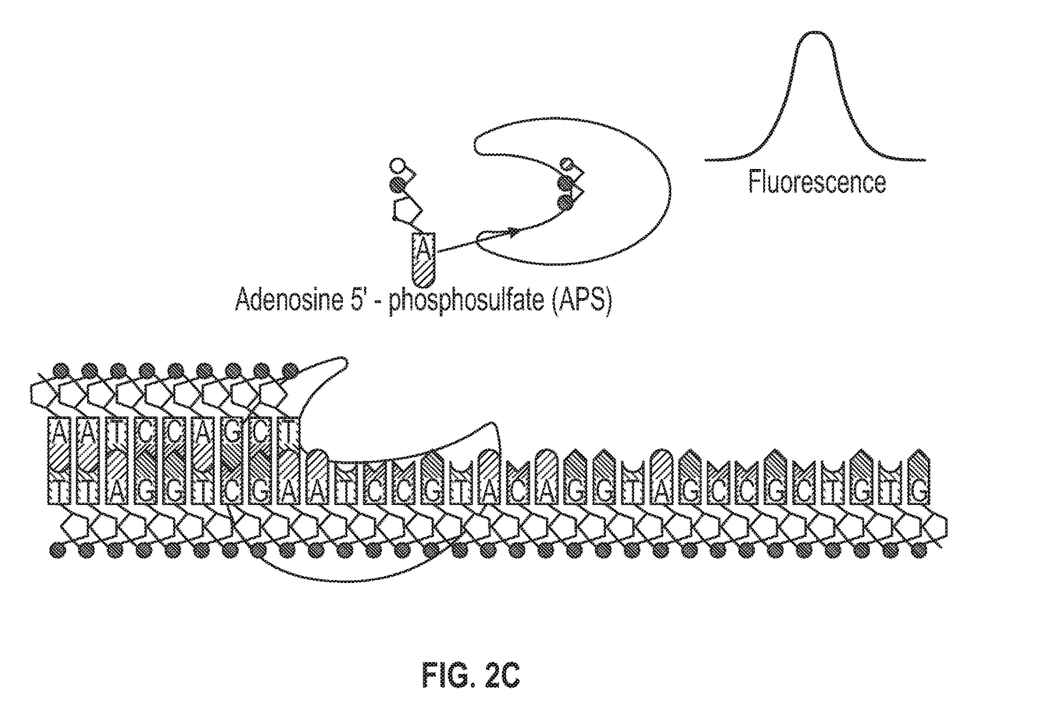
FIG. 2C further shows that during the nucleotide analog dNTP interaction with polymerase, fluorescence is generated upon cleavage of the labeled pyrophosphate generating a fluorescence signal corresponding to the color of the respective fluorophore. There is a unique colored fluorphore for each class of nucleotide analog dNTPs, such that each type of nucleotide analog has a different label.
Figure 3:
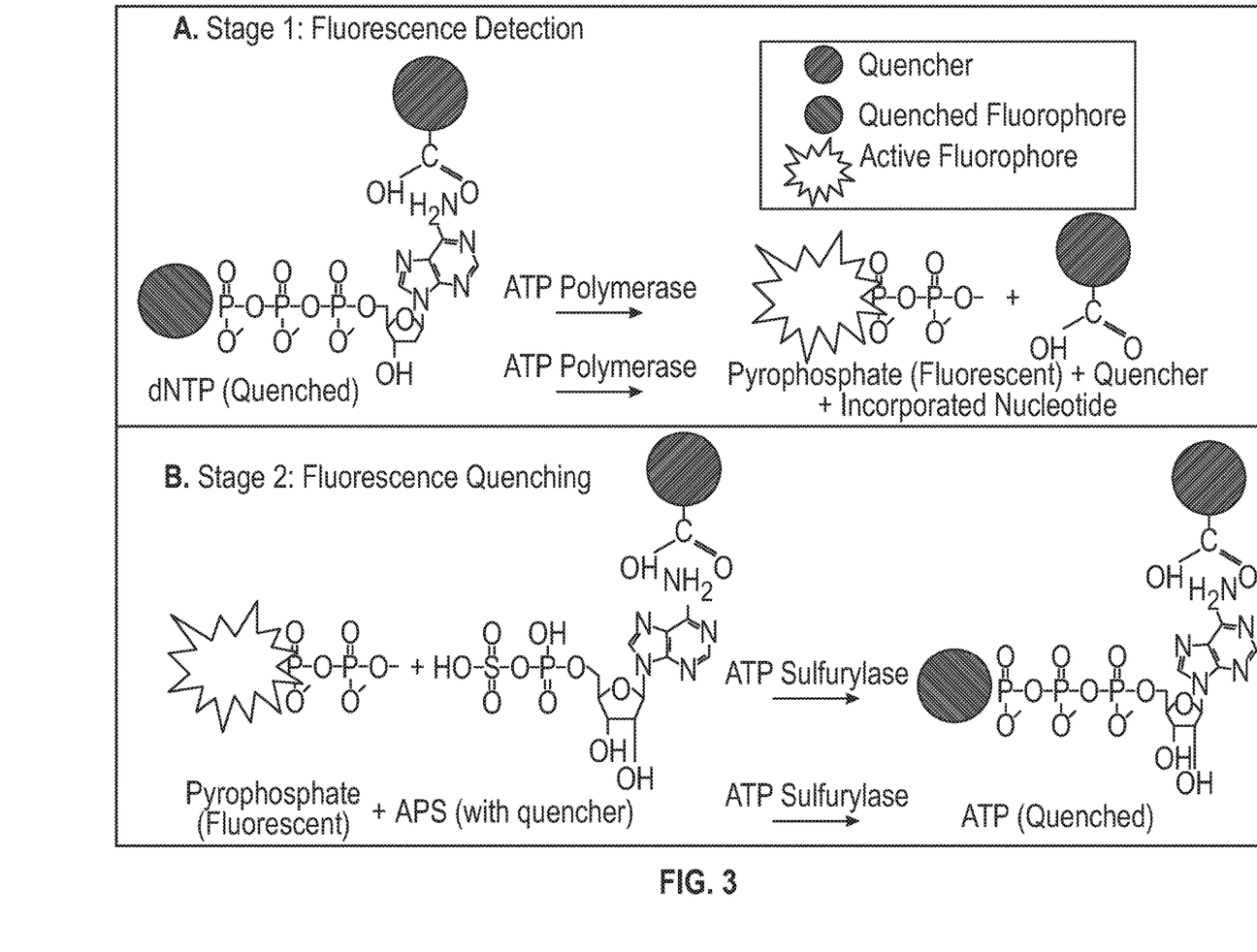
FIG. 3 shows the dual-quenching chemisty of an embodiment of the invention sequencing method that employs dual-quenching of an attached fluorophore, whereby the fluorophore is quenched by the respective nucleobase and an additional non-covalently bound quencher (A.) Stage 1: dNTP incorporation by polymerase and fluorescence generation via fluorescent labeled pyrophosphate release. (B.) Stage 2: Quenching of the released fluorescent pyrophosphate.

As used herein the phrase "requenching reaction" refers to any reaction that can requench a signal emitter, such as the released fluorophore in FIGS. 2B and 2C, or any other moiety emitting a signal to be detected herein. As set forth in the methods herein, the signals correspond to a particular nucleotide base in the DNA sequence. As used herein, "a component for a requenching reaction" can include a quenching enzyme, such as ATP sulfurylase, and the like.

The reaction conditions used can also influence the relative rates of the various reactions. Thus, controlling the reaction conditions can be useful in ensuring that the sequencing method is successful at calling the bases within the template at a high rate. The reaction conditions include, e.g., the type and concentration of buffer, the pH of the reaction, the temperature, the type and concentration of salts, the presence of particular additives which influence the kinetics of the enzyme, and the type, concentration, and relative amounts of various cofactors, including metal cofactors. Manipulation of reaction conditions to achieve or enhance two slow step behavior of polymerases is described in detail in U.S. Pat. No. 8,133,672, incorporated herein by reference.

Enzymatic reactions are often run in the presence of a buffer, which is used, in part, to control the pH of the reaction mixture. The type of buffer can in some cases influence the kinetics of the polymerase reaction in a way that can lead to two slow-step kinetics, when such kinetics are desired. For example, in some cases, use of IRIS as buffer is useful for obtaining a two slow-step reaction. Suitable buffers include, for example, TAPS (3-{[tris(hydroxymethyl)methyl]amino}propanesulfonic acid), Bicine (N,N-bis(2-hydroxyethyl)glycine), IRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction, and can be used as one of the polymerase reaction conditions to obtain a reaction exhibiting two slow-step kinetics. The pH can be adjusted to a value that produces a two slow-step reaction mechanism. The pH is generally between about 6 and about 9. In some embodiments, the pH is between about 6.5 and about 8.0. In other embodiments, the pH is between about 6.5 and 7.5. In particular embodiments, the pH is selected from about 6.5, 6.6, 6.7, 6.8, 6.9, 7.0, 7.1, 7.2, 7.3, 7.4, or 7.5.

The temperature of the reaction can be adjusted to ensure that the relative rates of the reactions are occurring in the appropriate range. The reaction temperature may depend upon the type of polymerase or selective cleaving activity employed. The temperatures used herein are also contemplated to manipulate and control the hydrogen bonding between two bases as well as the bases' interaction with the water in the reaction mixture, thereby controlling the solubility of the reaction components. The temperature with also affect the vinding efficiency of the non-covalently attached quenchers. In particular embodiments, temperatures between 15° C. and 90° C., between 20° C. and 50° C., between 20° C. and 40° C., or between 20° C. and 30° C. can be used.

In some embodiments, additives can be added to the reaction mixture that will influence the kinetics of the reaction. In some cases, the additives can interact with the active site of the enzyme, acting for example as competitive inhibitors. In some cases, additives can interact with portions of the enzyme away from the active site in a manner that will influence the kinetics of the reaction. Additives that can influence the kinetics include, for example, competitive but otherwise unreactive substrates or inhibitors in analytical reactions to modulate the rate of reaction as described in U.S. Utility Pat. No. 8,252,911, the full disclosure of which is incorporated herein by reference in its entirety for all purposes.

As another example, an isotope such as deuterium can be added to influence the rate of one or more step in the polymerase reaction. In some cases, deuterium can be used to slow one or more steps in the polymerase reaction due to the deuterium isotope effect. By altering the kinetics of steps of the polymerase reaction, in some instances two slow step kinetics, as described herein, can be achieved. The deuterium isotope effect can be used, for example, to control the rate of incorporation of nucleotide, e.g., by slowing the incorporation rate. Isotopes other than deuterium can also be employed, for example, isotopes of carbon (e.g. $^{13}C$), nitrogen, oxygen, sulfur, or phosphorous.

As yet another example, additives that can be used to control the kinetics of the polymerase reaction include the addition of organic solvents. The solvent additives are generally water soluble organic solvents. The solvents need not be soluble at all concentrations, but are generally soluble at the amounts used to control the kinetics of the polymerase reaction. While not being bound by theory, it is believed that the solvents can influence the three dimensional conformation of the polymerase enzyme which can affect the rates of the various steps in the polymerase reaction. For example, the solvents can affect steps involving conformational changes such as the isomerization steps. Added solvents can also affect, and in some cases slow, the translocation step. In some cases, the solvents act by influencing hydrogen bonding interactions.

The water miscible organic solvents that can be used to control the rates of one or more steps of the polymerase reaction in single molecule sequencing include, e.g., alcohols, amines, amides, nitriles, sulfoxides, ethers, and esters and small molecules having more than one of these functional groups. Exemplary solvents include alcohols such as methanol, ethanol, propanol, isopropanol, glycerol, and small alcohols. The alcohols can have one, two, three, or more alcohol groups. Exemplary solvents also include small molecule ethers such as tetrahydrofuran (THF) and dioxane, dimethylacetamide (DMA), dimethylsulfoxide (DMSO), dimethylformamide (DMF), and acetonitrile.

The water miscible organic solvent can be present in any amount sufficient to control the kinetics of the polymerase reaction. The solvents are generally added in an amount less than 40% of the solvent weight by weight or volume by volume. In some embodiments the solvents are added between about 0.1% and 30%, between about 1% and about 20%, between about 2% and about 15%, and between about 5% and 12%. The effective amount for controlling the kinetics can be determined by the methods described herein and those known in the art.

Another aspect of controlling the polymerase reaction conditions relates to the selection of the type, level, and relative amounts of cofactors. For example, during the course of the polymerase reaction, divalent metal co-factors, such as magnesium or manganese, will interact with the enzyme-substrate complex, playing a structural role in the definition of the active site. For a discussion of metal co-factor interactions in polymerase reactions, see, for example, Arndt, et al., Biochemistry (2001) 40:5368-5375. Suitable conditions include those described in U.S. Pat. No. 8,257,954, incorporated herein by reference in its entirety for all purposes.

In a particular embodiment of the invention methods, the rate and fidelity of the polymerase reaction is controlled by adjusting the concentrations of the dNTP nucleotide analogs such that the polymerase operates in near ideal conditions in terms of parameters such as substrate concentration, amount of optical excitation, level of chemical modification. Therefore, the polymerase enzyme is contemplated herein to reach its maximum read-lengths, e.g., approximately in the tens of thousands of base pairs, similar to the DNA synthesis lengths achieved in natural settings. This reduces device complexity and increases enzymatic sensitivity and specificity leading to low error-rates and thus low coverage. This not only reduces the cost of the device as well as cost per genome, but also makes applications such as single-nucleotide polymerism detection, structural variation, and genome assembly possible in a very compact system.

In another embodiment, as set forth above, because the quenching enzyme (e.g., ATP sulfurylase) and polymerase rates can vary significantly depending on the type and source of the enzymes, the rate of quenching achieved by the ATP sulfurylase reaction employed herein can be adjusted separately by adjusting reaction conditions such as ATP sulfurylase concentration.

The invention includes systems for sequencing of nucleic acid templates. The systems provide for concurrently sequencing a plurality of nucleic acid templates. The system can incorporate all of the reagents and methods described herein, and provides the instrumentation required for containing the sample, illuminating the sample with excitation light, detecting light emitted from the sample during sequencing to produce intensity versus time data from the labeled leaving groups cleaved from the nucleotide analogs as they are incorporated by the polymerase onto its congnate template dna and from the labeled leaving groups, e.g., fluorophore-labeled pyrophosphate, determining the sequence of a template using the sequential intensity versus time data.

As used herein, the phrase "detecting light" refers to well-known methods for detecting, for example, fluorescence emitted from fluorophore labels when such labels are in their excitation state emitting their respective signal.

The system for sequencing generally comprises a substrate having a plurality of single polymerase enzymes, single templates, or single primers within, for example, a unique droplet, or the like. In the case of highly processive enzyme polymerase reactions, each comprising a polymerase enzyme, a nucleic acid template, and a primer are uniquely confined such that their signals can be assigned to the respective nucleotide as gene synthesis occurs. The sequencing reagents generally include two or more types of nucleotide analogs, preferably four nucleotide analogs corresponding dATP, dATP, dAGP and dCTP, each nucleotide analog labeled with a different label. The polymerase sequentially adds nucleotides or nucleotide analogs to the growing strand, which extends from the primer. Each added nucleotide or nucleotide analog is complementary to the corresponding base on the template nucleic acid, such that the portion of the growing strand that is produced is complementary to the template.

The system comprises illumination optics for illuminating the labeled leaving groups from the respective dNTPs as they are incorporated into the template strand, e.g., labeled pyrophosphates. The illumination optics illuminate the labeled leaving groups in a wavelength range that will excite the labels on the cleaved pyrophosphate (no longer quenched by the nucleobase).

The system further comprises detection optics for observing signals from the labeled leaving groups cleaved from the respective dNTP during the polymerase enzyme mediated addition to the template strand. The detection optics observe a plurality of single molecule polymerase sequencing reactions concurrently, observing the nucleotide or nucleotide analog additions for each of them via the labeled leaving group (e.g., fluorophore-labeled pyrophosphate; PP). For each of the observed single molecule polymerase sequencing reactions, the detection optics concurrently observe the signals from each of the labeled leaving groups that are indicative of the respective unquenched fluorophore-labeled corresponding to a respective dNTP, until each respective signal is quenched by the quenching enzyme (e.g., ATP sulfurylase).

The system also comprises a computer configured to determine the type of nucleotide analog that is added to the growing strand using the observed signal from the respective leaving group; whereby observed signals from the labeled leaving group are used to indicate whether a type of nucleotide or nucleotide analog is incorporated into the growing strand. The computer generally receives information regarding the observed signals from the detection optics in the form of signal data. The computer stores, processes, and interprets the signal data, using the signal data in order to produce a sequence of base calls. The base calls represent the computers estimate of the sequence of the template from the signal data received combined with other information given to the computer to assist in the sequence determination.

Optical illumination and detections systems which can be used with the present invention are described, for example in U.S. Pat. Nos. 8,802,424; 7,714,303; and 7,820,983, each of which are incorporated herein by reference in their entirety for all purposes.

Computers for use in carrying out the processes of the invention can range from personal computers such as PC or Macintosh®. type computers running Intel Pentium or Duo-Core processors, to workstations, laboratory equipment, or high speed servers, running UNIX, LINUX, Windows®., or other systems, Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other sequencing specific formats including "fastq" or the "qseq" format (Illumina); while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

In some embodiments of the methods and systems of the invention, optical confinements are used to enhance the ability to concurrently observe multiple single molecule polymerase sequencing reactions simultaneously. In general, optical confinements are disposed upon a substrate and used to provide electromagnetic radiation to or derive such radiation from only very small spaces or volumes. Such optical confinements may comprise structural confinements, e.g., wells, recesses, conduits, or the like, or they may comprise optical processes in conjunction with other components, to provide illumination to or derive emitted radiation from only very small volumes. Examples of such optical confinements include systems that utilize, e.g., total internal reflection (TIR) based optical systems whereby light is directed through a transparent portion of the substrate at an angle that yields total internal reflection within the substrate.

In a particular embodiment, a preferred optical confinement is a micro-droplet which can contain and individual sequencing reaction set forth herein. For example, the sequencing mixture reaction ingredients can be split in a way that each micro-droplet contains one polymerase and one template nucleic acid whereby each signal detection unit is focused on a single micro-droplet. It is contemplate herein that each micro-droplet is a single molecule reaction cell containing individual single molecule sequencing reactions. The micro-droplet reaction cell is also advantageously useful in the invention sequencing methods to act as micro-lenses to focus light on the reaction and to the respective signal detection unit.

The substrates of the invention are generally rigid, and often planar, but need not be either. Where the substrate comprises an array of optical confinements, the substrate will generally be of a size and shape that can interface with optical instrumentation to allow for the illumination and for the measurement of light from the optical confinements. Typically, the substrate will also be configured to be held in contact with liquid media, for instance containing reagents and substrates and/or labeled components, such as the fluorophore-labeled pyrophosphates, for optical measurements.

Where the substrates comprise arrays of optical confinements, the arrays may comprise a single row or a plurality of rows of optical confinement on the surface of a substrate, where when a plurality of lanes are present, the number of lanes will usually be at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to form a grid, or to form a circular, elliptical, oval, conical, rectangular, triangular, or polyhedral pattern. To minimize the nearest-neighbor distance between adjacent optical confinements, a hexagonal array is sometimes preferred.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter plate wherein each micro well of the plate contains a subject array of optical confinements.

In accordance with the invention, arrays of confinements (e.g., reaction cells, micro-droplets, and the like) are provided in arrays of more than 100, more than 1000, more than 10,000, more that 100,000, or more than 1,000,000 separate reaction cells (such as a micro-droplet or the like) on a single substrate. In addition, the reaction cell arrays are typically comprised in a relatively high density on the surface of the substrate. Such high density typically includes reaction cells present at a density of greater than 10 reaction cells per $mm^2$, preferably, greater than 100 reaction cells per $mm^2$ of substrate surface area, and more preferably, greater than 500 or even 1000 reaction cells per $mm^2$ and in many cases up to or greater than 100,000 reaction cells per mm $mm^2$. Although in many cases, the reaction cells in the array are spaced in a regular pattern, e.g., in 2, 5, 10, 25, 50 or 100 or more rows and/or columns of regularly spaced reaction cells in a given array, in certain preferred cases, there are advantages to providing the organization of reaction cells in an array deviating from a standard row and/or column format. In preferred aspects, the substrates include as the particular reaction cell micro-droplets as the optical confinements to define the discrete single molecule sequencing reaction regions on the substrate.

The overall size of the array of optical confinements can generally range from a few nanometers to a few millimeters in thickness, and from a few millimeters to 50 centimeters in width and/or length. Arrays may have an overall size of about few hundred microns to a few millimeters in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements may be placed close to each other relative to the incident wavelength.

The individual confinement in the array can provide an effective observation volume less than about 1000 zeptoliters, less than about 900, less than about 200, less than about 80, less than about 10 zeptoliters. Where desired, an effective observation volume less than 1 zeptoliter can be provided. In a preferred aspect, the individual confinement yields an effective observation volume that permits resolution of individual molecules, such as enzymes, present at or near a physiologically relevant concentration. The physiologically relevant concentrations for many biochemical reactions range from micro-molar to millimolar because most of the enzymes have their Michaelis constants in these ranges. Accordingly, preferred array of optical confinements has an effective observation volume for detecting individual molecules present at a concentration higher than about 1 micromolar (uM), or more preferably higher than 50 uM, or even higher than 100 uM. In particular embodiments, typical microdroplet sizes range from 10 micrometers to 200 micrometers, and thus typical microdroplet volumes are around 5 picoliters to 20 nanoliters.

In the context of chemical or biochemical analyses within optical confinements, it is generally desirable to ensure that the reactions of interest are taking place within the optically interrogated portions of the confinement, at a minimum, and preferably such that only the reactions of a single molecule polymerase sequencing reaction is occurring within an interrogated portion of an individual confinement (e.g., within a micro-droplet, or the like). A number of methods may generally be used to provide individual molecules within the observation volume. A variety of these are described in U.S. Pat. No. 7,763,423, incorporated herein by reference in its entirety for all purposes, which describes, inter alia, modified surfaces that are designed to immobilize individual molecules to the surface at a desired density, such that approximately one, two, three or some other select number of molecules would be expected to fall within a given observation volume. Typically, such methods utilize dilution techniques to provide relatively low densities of coupling groups on a surface, either through dilution of such groups on the surface or dilution of intermediate or final coupling groups that interact with the molecules of interest, or combinations of these. Also contemplated herein is the use of these dilution techniques for providing one, two, three or some other select number of single molecule sequencing reactions to fall within a given observation volume without being immobilized to a surface, such as would occur in the micro-droplet reaction cell contemplated herein for optical confinement. In a particular embodiment, the dilution techniques are utilized to provide a one single molecule sequencing reaction in a micro-droplet for use in the invention sequencing method.

The systems and methods of the inventions can result in improved sequence determination and improved base calling by monitoring the signal from the labeled leaving groups of the nucleotide analogs, e.g., a polyphosphate label, using systems well-known in the art. In general, signal data is received by the processor. The information received by the processor can come directly from the detection optics, or the signal from the detection optics can be treated by other processors before being received by the processor. A number of initial calibration operations may be applied. Some of these initial calibration steps may be performed just once at the beginning of a run or on a more continuous basis during the run. These initial calibration steps can include such things as centroid determination, alignment, gridding, drift correction, initial background subtraction, noise parameter adjustment, frame-rate adjustment, etc. Some of these initial calibration steps, such as binning, may involve communication from the processor back to the detector/camera, as discussed further below.

Generally, some type of spectral trace determination, spectral trace extraction, or spectral filters are applied to the initial signal data. Some or all of these filtration steps may optionally be carried out at a later point in the process, e.g., after the pulse identification step. The spectral trace extraction/spectral filters may include a number of noise reduction and other filters as is well-known in the art. Spectral trace determination is performed at this stage for many of the example systems discussed herein because the initial signal data received are the light levels, or photon counts, captured by a series of adjacent pixel detectors. For example, in one example system, pixels (or intensity levels) from positions are captured for an individual wave-guide at each frame. Light of different frequencies or spectrum will fall on more than one of the positions and there is generally some overlap and possibly substantial overlap. According to specific embodiments of the invention, spectral trace extraction may be performed using various type of analyses, as discussed below, that provide the highest signal-to-noise ratio for each spectral trace.

As an alternative to a spectral trace determination, methods of the invention may also analyze a single signal derived from the intensity levels at the multiple pixel positions (this may be referred to as a summed spectral signal or a gray-scale spectral signal or an intensity level signal). In many situations, it has been found that spectral extraction, however, provides better SNR (signal to noise ratio) and therefore pulse detection when extracted spectral traces are analyzed for pulses somewhat separately. In further embodiments, a method according to the invention may analyze the multiple captured pixel data using a statistical model such as a Hidden Markov Model. In the invention sequencing methods and systems provided herein, determining multiple (e.g., four) spectral traces from the initial signal data is a preferred method.

Whether the signal from the labeled leaving groups can be categorized as a significant signal pulse or event is determined. In some example systems, because of the small number of photons available for detection and because of the speed of detection, various statistical analysis techniques may be performed in determining whether a significant pulse has been detected.

If the signal is identified as a significant pulse or signal event, a further optional spectral profile comparison may be performed to verify the spectral assignment. This spectral profile comparison is optional in embodiments where spectral traces are determined prior to or during pulse identification. Once a color is assigned to a given incorporation signal (e.g., a fluorophore-labeled dNTP\), that assignment is used to call either the respective base incorporated, or its complement in the template sequence. In order to make this determination, the signals coming from the channel corresponding to the labeled leaving group are used to assess whether a pulse from a nucleotide label corresponds to an incorporation event. The compilation of called bases is then subjected to additional processing to provide linear sequence information, e.g., the successive sequence of nucleotides in the template sequence, assemble sequence fragments into longer contigs, or the like.

As noted above, the signal data is input into the processing system, e.g., an appropriately programmed computer or other processor. Signal data may input directly from a detection system, e.g., for real time signal processing, or it may be input from a signal data storage file or database. In some cases, e.g., where one is seeking immediate feedback on the performance of the detection system, adjusting detection or other experimental parameters, real-time signal processing will be employed. In some embodiments, signal data is stored from the detection system in an appropriate file or database and is subject to processing in post reaction or non-real time fashion.

The signal data used in conjunction with the present invention may be in a variety of forms. For example, the data may be numerical data representing intensity values for optical signals received at a given detector or detection point of an array based detector. Signal data may comprise image data from an imaging detector, such as a CCD, EMCCD, ICCD or CMOS sensor. In particular embodiments, for detecting low numbers of photons from single molecules, the use of a photomultiplier tube (PMT) and/or a photon counter unit is contemplated for use in the invention methods. In either event, signal data used according to specific embodiments of the invention generally includes both intensity level information and spectral information. In the context of separate detector elements, such spectral information will generally includes identification of the location or position of the detector portion (e.g., a pixel) upon which an intensity is detected. In the context of image data, the spectral image data will typically be the data derived from the image data that correlates with the calibrated spectral image data for the imaging system and detector when the system includes spectral resolution of overall signals. The spectral data may be obtained from the image data that is extracted from the detector, or alternatively, the derivation of spectral data may occur on the detector such that spectral data will be extracted from the detector.

For the sequencing methods described above, there will be a certain amount of optical signal that is detected by the detection system that is not the result of a signal from an incorporation event. Such signal will represent "noise" in the system, and may derive from a number of sources that may be internal to the monitored reaction, internal to the detection system and/or external to all of the above. The practice of the present invention advantageously reduces these overall sources of noise typically present in prior art methods. Examples of prior art noise internal to the reaction that is advantageously reduced in accordance with the present invention includes, e.g.: presence of fluorescent labels that are not associated with a detection event, e.g., liberated labels, labels associated with unincorporated bases in diffused in solution, bases associated with the complex but not incorporated; presence of multiple complexes in an individual observation volume or region; non-specific adsorption of dyes or nucleotides to a substrate or enzyme complex within an observation volume; contaminated nucleotide analogs, e.g., contaminated with other fluorescent components; other reaction components that may be weakly fluorescent; spectrally shifting dye components, e.g., as a result of reaction conditions; and the like. The controlled use of fluorescent signal detection and information from the fluorescent label on the leaving group of the respective dNTP that then becomes quenched prior to the incorporation of the next nucleotide analog advantageously provides a way of reducing or eliminating sources of noise, thereby improving the signal to noise of the system, and improving the quality of the base calls and associated sequence determination.

Sources of noise internal to the detection system, but outside of the reaction mixture can include, e.g., reflected excitation radiation that bleeds through the filtering optics; scattered excitation or fluorescent radiation from the substrate or any of the optical components; spatial cross-talk of adjacent signal sources; auto-fluorescence of any or all of the optical components of the system; read noise from the detector, e.g., CCDs, gain register noise, e.g., for EMCCD cameras, and the like. Other system derived noise contributions can come from data processing issues, such as background correction errors, focus drift errors, autofocus errors, pulse frequency resolution, alignment errors, and the like. Still other noise contributions can derive from sources outside of the overall system, including ambient light interference, dust, and the like.

These noise components contribute to the background photons underlying any signal pulses that may be associated with an incorporation event. As such, the noise level will typically form the limit against which any signal pulses may be determined to be statistically significant.

Identification of noise contribution to overall signal data may be carried out by a number of methods, including, for example, signal monitoring in the absence of the reaction of interest, where any signal data is determined to be irrelevant. Alternatively, and preferably, a baseline signal is estimated and subtracted from the signal data that is produced by the system, so that the noise measurement is made upon and contemporaneously with the measurements on the reaction of interest. Generation and application of the baseline may be carried out by a number of means, which are described in greater detail below.

In accordance with the present invention, signal processing methods distinguish between noise, as broadly applied to all non-significant pulse based signal events, and significant signal pulses that may, with a reasonable degree of confidence, be considered to be associated with, and thus can be tentatively identified as, an incorporation event. In the context of the present invention, a signal event is first classified as to whether it constitutes a significant signal pulse based upon whether such signal event meets any of a number of different pulse criteria. Once identified or classified as a significant pulse, the signal pulse may be further assessed to determine whether the signal pulse constitutes an incorporation event and may be called as a particular incorporated base. As will be appreciated, the basis for calling a particular signal event as a significant pulse, and ultimately as an incorporation event, will be subject to a certain amount of error, based upon a variety of parameters as generally set forth herein. As such, it will be appreciated that the aspects of the invention that involve classification of signal data as a pulse, and ultimately as an incorporation event or an identified base, are subject to the same or similar errors, and such nomenclature is used for purposes of discussion and as an indication that it is expected with a certain degree of confidence that the base called is the correct base in the sequence, and not as an indication of absolute certainty that the base called is actually the base in a given position in a given sequence.

One such signal pulse criterion is the ratio of the signals associated with the signal event in question to the level of all background noise ("signal to noise ratio" or "SNR"), which provides a measure of the confidence or statistical significance with which one can classify a signal event as a significant signal pulse. In distinguishing a significant pulse signal from systematic or other noise components, the signal generally must exceed a signal threshold level in one or more of a number of metrics, including for example, signal intensity, signal duration, temporal signal pulse shape, pulse spacing, and pulse spectral characteristics.

By way of a simplified example, signal data may be input into the processing system. If the signal data exceeds a signal threshold value in one or more of signal intensity and signal duration, it may be deemed a significant pulse signal. Similarly, if additional metrics are employed as thresholds, the signal may be compared against such metrics in identifying a particular signal event as a significant pulse. As will be appreciated, this comparison will typically involve at least one of the foregoing metrics, and preferably at least two such thresholds, and in many cases three or all four of the foregoing thresholds in identifying significant pulses.

Signal threshold values, whether in terms of signal intensity, signal duration, pulse shape, spacing or pulse spectral characteristics, or a combination of these, will generally be determined based upon expected signal profiles from prior experimental data, although in some cases, such thresholds may be identified from a percentage of overall signal data, where statistical evaluation indicates that such thresholding is appropriate. In particular, in some cases, a threshold signal intensity and/or signal duration may be set to exclude all but a certain fraction or percentage of the overall signal data, allowing a real-time setting of a threshold. Again, however, identification of the threshold level, in terms of percentage or absolute signal values, will generally correlate with previous experimental results. In alternative aspects, the signal thresholds may be determined in the context of a given evaluation. In particular, for example, a pulse intensity threshold may be based upon an absolute signal intensity, but such threshold would not take into account variations in signal background levels, e.g., through reagent diffusion, that might impact the threshold used, particularly in cases where the signal is relatively weak compared to the background level. As such, in certain aspects, the methods of the invention determine the background fluorescence of the particular reaction in question, which is relatively small because the contribution of freely diffusing dyes or dye labeled analogs into a micro-droplet is minimal or nonexistent, and sets the signal threshold above that actual background by the desired level, e.g., as a ratio of pulse intensity to background fluorophore diffusion, or by statistical methods, e.g., 5 sigma, or the like. By correcting for the actual reaction background, such as the minimal fluorophore diffusion background, the threshold is automatically calibrated against influences of variations in dye concentration, laser power, or the like. By reaction background is meant the level of background signal specifically associated with the reaction of interest and that would be expected to vary depending upon reaction conditions, as opposed to systemic contributions to background, e.g., autofluorescence of system or substrate components, laser bleedthrough, or the like.

In particularly preferred aspects that rely upon real-time detection of incorporation events, identification of a significant signal pulse may rely upon a signal profile that traverses thresholds in both signal intensity and signal duration. For example, when a signal is detected that crosses a lower intensity threshold in an increasing direction, ensuing signal data from the same set of detection elements, e.g., pixels, are monitored until the signal intensity crosses the same or a different intensity threshold in the decreasing direction. Once a peak of appropriate intensity is detected, the duration of the period during which it exceeded the intensity threshold or thresholds is compared against a duration threshold. Where a peak comprises a sufficiently intense signal of sufficient duration, it is called as a significant signal pulse.

In addition to, or as an alternative to using the intensity and duration thresholds, pulse classification may employ a number of other signal parameters in classifying pulses as significant. Such signal parameters include, e.g., pulse shape, spectral profile of the signal, e.g., pulse spectral centroid, pulse height, pulse diffusion ratio, pulse spacing, total signal levels, and the like.

Either following or prior to identification of a significant signal pulse, signal data may be correlated to a particular signal type. In the context of the optical detection schemes used in conjunction with the invention, this typically denotes a particular spectral profile of the signal giving rise to the signal data. In particular, the optical detection systems used in conjunction with the methods and processes of the invention are generally configured to receive optical signals that have distinguishable spectral profiles, where each spectrally distinguishable signal profile may generally be correlated to a different reaction event. In the case of nucleic acid sequencing, for example, each spectrally distinguishable signal may be correlated or indicative of a specific nucleotide incorporated or present at a given position of a nucleic acid sequence. Consequently, the detection systems include optical trains that receive such signals and separate the signals based upon their spectra. The different signals are then directed to different detectors, to different locations on a single array based detector, or are differentially imaged upon the same imaging detector (See, e.g., U.S. Pat. No. 7,805,081, which is incorporated herein by reference in its entirety for all purposes).

In the case of systems that employ different detectors for different signal spectra, assignment of a signal type (for ease of discussion, referred to hereafter as "color classification" or "spectral classification") to a given signal is a matter of correlating the signal pulse with the detector from which the data derived. In particular, where each separated signal component is detected by a discrete detector, a signal's detection by that detector is indicative of the signal classifying as the requisite color.

In preferred aspects, however, the detection systems used in conjunction with the invention utilize an imaging detector upon which all or at least several of the different spectral components of the overall signal are imaged in a manner that allows distinction between different spectral components. Thus, multiple signal components are directed to the same overall detector, but may be incident upon wholly or partly different regions of the detector, e.g., imaged upon different sets of pixels in an imaging detector, and give rise to distinguishable spectral images (and associated image data). As used herein, spectra or spectral image generally indicates a pixel image or frame (optionally data reduced to one dimension) that has multiple intensities caused by the spectral spread of an optical signal received from a reaction location.

In its simplest form, it will be understood that assignment of color to a signal event incident upon a group of contiguous detection elements or pixels in the detector would be accomplished in a similar fashion as that set forth for separate detectors. In particular, the position of the group of pixels upon which the signal was imaged, and from which the signal data is derived, is indicative of the color of the signal component. In particularly preferred aspects, however, spatial separation of the signal components may not be perfect, such that signals of differing colors are imaged on overlapping sets of pixels. As such, signal identification will generally be based upon the aggregate identity of multiple pixels (or overall image of the signal component) upon which a signal was incident.

Once a particular signal is identified as a significant pulse and is assigned a particular spectrum, the spectrally assigned pulse may be further assessed to determine whether the pulse can be called an incorporation event and, as a result, call the base incorporated in the nascent strand, or its complement in the template sequence. Signals from the labeled leaving group (e.g., fluorophore labeled pyrophosphate) are used to identify which base should be called. As set forth above, in one embodiment, by using two quenchers per nucleotide analog, such as the nucleobase of the nucleotide and a non-covalently attached quencher, a set of characteristic signals are produced which can be correlated with high confidence to an incorporation event.

In addition, calling of bases from color assigned pulse data will typically employ tests that again identify the confidence level with which a base is called. Typically, such tests will take into account the data environment in which a signal was received, including a number of the same data parameters used in identifying significant pulses. For example, such tests may include considerations of background signal levels, adjacent pulse signal parameters (spacing, intensity, duration, etc.), spectral image resolution, and a variety of other parameters. Such data may be used to assign a score to a given base call for a color assigned signal pulse, where such scores are correlative of a probability that the base called is incorrect, e.g., 1 in 100 (99% accurate), 1 in 1000 (99.9% accurate), 1 in 10,000 (99.99% accurate), 1 in 100,000 (99.999% accurate), or even greater. Similar to PHRED or similar type scoring for chromatographically derived sequence data, such scores may be used to provide an indication of accuracy for sequencing data and/or filter out sequence information of insufficient accuracy.

Once a base is called with sufficient accuracy, subsequent bases called in the same sequencing run, and in the same primer extension reaction, may then be appended to each previously called base to provide a sequence of bases in the overall sequence of the template or nascent strand. Iterative processing and further data processing can be used to fill in any blanks, correct any erroneously called bases, or the like for a given sequence.

Analysis of sequencing-by-incorporation-reactions on an array of reaction locations according to specific embodiments of the invention can be conducted as illustrated graphically in FIG. 13 of U.S. Pat. No. 9,447,464, incorporated by reference in its entirety for all purposes). For example, data captured by a camera is represented as a movie, which is also a time sequence of spectra. Spectral calibration templates are used to extract traces from the spectra. Pulses identified in the traces are then used to return to the spectra data and from that data produce a temporally averaged pulse spectrum for each pulse, such pulse spectra will include spectra for events relating to enzyme conformational changes. The spectral calibration templates are then also used to classify pulse spectrum to a particular base. Base classifications and pulse and trace metrics are then stored or passed to other logic for further analysis. The downstream analysis will include using the information from enzyme conformational changes to assist in the determination of incorporation events for base calling. Further base calling and sequence determination methods for use in the invention can include those described in, for sample, U.S. Pat. No. 8,182,993, which is incorporated herein by reference in its entirety for all purposes.

EXAMPLES

Single Molecule Sequencing

Prior to undergoing a single molecule sequencing reaction, the respective fluorophores are attached to the terminal phosphate of its corresponding dNTP for each of dATP, dTTP, dGTP and dCTP, which fluorophore is quenched by the nucleobase while it is attached to the dNTP. Each nucleobase has a different quenching capability for the different fluorophores (FIG. 2.A). During the single molecule sequencing reaction, upon interaction with the DNA polymerase, while the DNA polymerase binds the dNTP nucleotide analog to the template strand, it cleaves off a pyrophosphate that has the signaling fluorophore attached thereto (FIG. 2.B).

As a result of dNTP interacting with the DNA polymerase, fluorescence light is generated upon cleavage of labeled pyrophosphate generating a fluorescence signal corresponding to the color of the fluorophore selected for the particular dNTP. There is a different fluorophore for each dNTP base (A, T, G, C) (FIG. 2.C). The respective fluorescent light is the detected prior to the light becoming quenched.

Figure 2D:
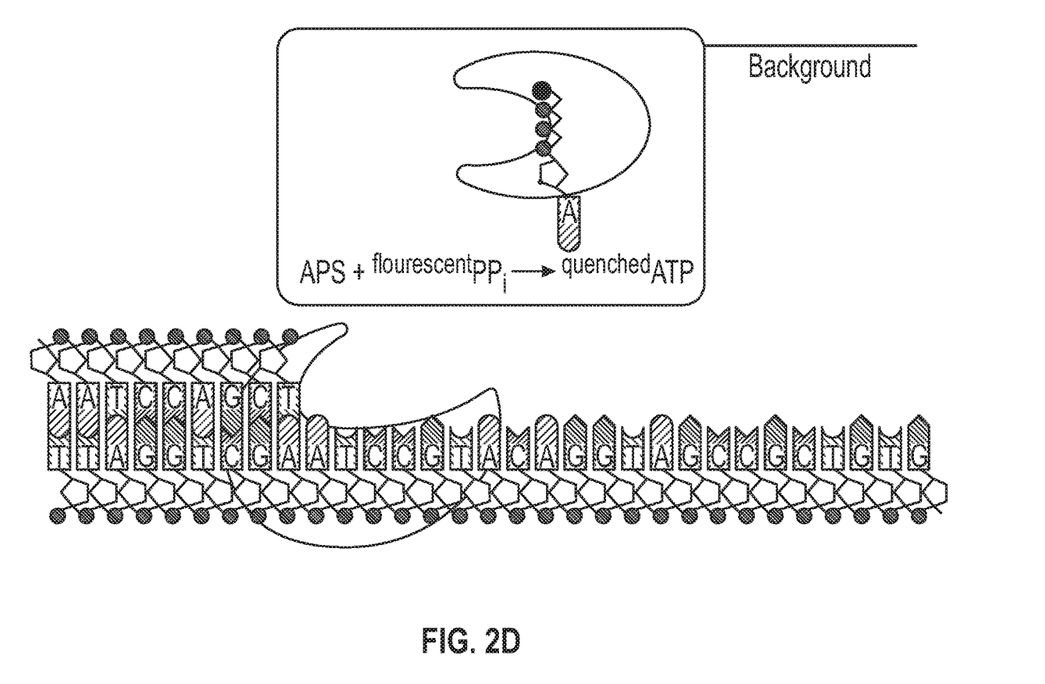
FIG. 2D shows that after the labeled pyrophosphate is released from its respective dNTP, it next interacts with ATP sulfurylase, which binds the respective labeled pyrophosphate to to adenosine 5'-phosphosulfate (APS) resulting in quenching of the fluorophore by adenine upon its binding, thereby substantially reducing fluorescence background noise.

Once released and its fluorescent light has been detected, the labeled pyrophosphate ($PP_i$) interacts with ATP sulfurylase, which binds the labeled pyrophosphate to adenosine 5'-phosphosulfate (APS) resulting in the quenching of the fluorophore by adenine upon binding. The quenching of the fluorophore labels on the pyrophosphates substantially eliminates all background fluorescent signals in the sequencing mixture (FIG. 2.D).

This dNTP incorporation process is repeated until the desired nucleic acid read-length has been achieved.

While the present embodiments have been particularly shown and described with reference to example embodiments herein, it will be understood by those of ordinary skill in the art that various changes in form and details may be made therein without departing from the spirit and scope of the present embodiments as defined by the following claims. Those skilled in the art will recognize, or be able to ascertain using no more than routine experimentation, numerous equivalents to the specific procedures described herein. Such equivalents are considered to be within the scope of the present invention and are covered by the following claims. The contents of all non-patent literature publications, patents, and patent applications cited throughout this application are hereby incorporated by reference in their entirety for all purposes. The appropriate components, processes, and methods of those patents, applications and other documents may be selected for the present invention and embodiments thereof.

What is claimed is:

1. A method for sequencing a nucleic acid template comprising:
providing a sequencing mixture comprising (i) a polymerase enzyme, (ii) a template nucleic acid, and (iii) a polymerase reagent solution having the components for carrying out template directed synthesis of a growing nucleic acid strand, wherein said polymerase reagent solution includes a component for a requenching reaction and a plurality of types of nucleotide analogs; wherein each type of nucleotide analog has a labeled leaving group that is cleavable by the polymerase, and each type of nucleotide analog has a different label, wherein the labeled leaving group is cleaved upon polymerase-dependent binding of a respective nucleotide analog to the template strand;
carrying out nucleic acid synthesis such that a plurality of nucleotide analogs are added sequentially to the template whereby: a) a nucleotide analog associates with the polymerase, b) the nucleotide analog is incorporated on the template strand by the polymerase when the labeled leaving group on that nucleotide analog is cleaved by the polymerase, wherein the labeled leaving group emits light upon cleavage, then c) the labeled leaving group on the nucleotide analog is quenched by the requenching reaction, wherein a removable quencher molecule is attached to the nucleotide analog through electrostatic interaction or hydrogen bonding to achieve dual-quenching; and
detecting light from the labels while nucleic acid synthesis is occurring, and using light detected in the time between step b) when the labelled leaving group is cleaved, and step c) in which the labeled leaving group is quenched, to determine a sequence of the template nucleic acid.

2. The method of claim 1, wherein the nucleotide analog has been modified by a fluorophore attached to a terminal phosphate.

3. The method of claim 1, wherein the leaving group is a labelled pyrophosphate.

4. The method of claim 3, wherein the pyrophosphate is labeled with a fluorophore.

5. The method of claim 1, wherein each base of a nucleotide is labeled with a unique fluorophore relative to other bases.

6. The method of claim 1, wherein the requenching reaction uses a quenching enzyme or Plasmonics.

7. The method of claim 6, wherein the quenching enzyme is ATP sulfurylase.

8. The method of claim 1, wherein requenching is achieved by an adenosine nucleobase on APS.

9. The method of claim 1, wherein the polymerase enzyme is DNA polymerase.

10. The method of claim 1, wherein types of nucleotide analogs comprise dATP, dTTP, dGTP, dCTP and dUTP.

11. The method of claim 1, wherein the requenching reaction uses plasmonics.

12. The method of claim 2, wherein the fluorophore is quenched by the nucleobase on the nucleotide.

13. The method of claim 1, wherein the removable quencher molecule is attached to the nucleotide analog at the nucleobase or sugar.

* * * * *